US010078206B2

(12) United States Patent
Kalkbrenner et al.

(10) Patent No.: US 10,078,206 B2
(45) Date of Patent: *Sep. 18, 2018

(54) HIGH-RESOLUTION MICROSCOPE AND IMAGE SPLITTER ARRANGMENT

(71) Applicant: Carl Zeiss Microscopy GmbH, Jena (DE)

(72) Inventors: Thomas Kalkbrenner, Jena (DE); Michael Goelles, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 106 days.

This patent is subject to a terminal disclaimer.

(21) Appl. No.: 15/087,177

(22) Filed: Mar. 31, 2016

(65) Prior Publication Data

US 2016/0216502 A1    Jul. 28, 2016

Related U.S. Application Data

(63) Continuation of application No. 13/518,108, filed as application No. PCT/EP2010/007594 on Dec. 14, 2010, now Pat. No. 9,372,333.

(30) Foreign Application Priority Data

Dec. 22, 2009  (DE) .................. 10 2009 060 490

(51) Int. Cl.
*G02B 21/36*  (2006.01)
*G02B 21/00*  (2006.01)
(Continued)

(52) U.S. Cl.
CPC ....... *G02B 21/361* (2013.01); *G01N 21/6458* (2013.01); *G02B 17/023* (2013.01);
(Continued)

(58) Field of Classification Search
None
See application file for complete search history.

(56) References Cited

U.S. PATENT DOCUMENTS 5,982,497 A * 11/1999 Hopkins ............... G01J 3/02
250/226
9,372,333 B2 * 6/2016 Kalkbrenner ...... G02B 21/0076
2005/0057796 A1 * 3/2005 Shafer ................ G02B 17/023
359/357

FOREIGN PATENT DOCUMENTS

AT        402 863 B      9/1997
DE     28 34 204 A1     3/1980
(Continued)

OTHER PUBLICATIONS

Eric Betzig, et al., "Imaging Intracellular Fluorescent Proteins at Nanometer Resolution", *Science* (2006), 313:1642-1645.
(Continued)

*Primary Examiner* — Anand S Rao
*Assistant Examiner* — Tyler B Edwards
(74) *Attorney, Agent, or Firm* — Duane Morris LLP

(57) ABSTRACT

The invention relates to a microscope having an illumination beam path with wide field illumination of a sample and a first detection beam path having a spatially resolved surface receiver, which is reached by a first part of the detection light coming from the sample via the first detection beam path, or an image divider assembly for a microscope. In order to lengthen the optical path length, at least a second part of the detection light coming from the sample is masked out of the detection beam path and, via deflection means belonging to the detection beam path, is led into a second detection beam path and, preferably via further deflection means, is deflected back in the direction of the detection in such a way that detection light is applied to at least two partial regions beside one another on the surface receiver. At least the
(Continued)

second part of the detection light runs in an optical element having an optical density that is increased as compared with the first detection beam path, in order to lengthen the optical path length, and the optical element is designed to be displaceable at an angle, preferably perpendicular, to the optical axis of the first detection beam path in order to adjust the optical path length, and has flat surfaces, at least on the light entry and light exit side thereof; a prism is provided, preferably a glass prism, preferably at least in the second detection beam path after a first beam deflection, for deflection in a direction parallel to the first detection beam path, in order to increase the path length and for reverse deflection.

16 Claims, 3 Drawing Sheets

(51) Int. Cl.

| | | |
|---|---|---|
| G01N 21/64 | (2006.01) | |
| G02B 21/18 | (2006.01) | |
| G02B 17/02 | (2006.01) | |
| G02B 21/16 | (2006.01) | |
| G02B 27/10 | (2006.01) | |
| G02B 27/14 | (2006.01) | |
| G02B 27/58 | (2006.01) | |
| G02B 7/38 | (2006.01) | |
| G02B 21/24 | (2006.01) | |

(52) U.S. Cl.
CPC ..... *G02B 21/0032* (2013.01); *G02B 21/0072* (2013.01); *G02B 21/0076* (2013.01); *G02B 21/16* (2013.01); *G02B 21/18* (2013.01); *G02B 21/367* (2013.01); *G02B 27/106* (2013.01); *G02B 27/1066* (2013.01); *G02B 27/141* (2013.01); *G02B 27/144* (2013.01); *G02B 27/145* (2013.01); *G02B 27/58* (2013.01); *G02B 7/38* (2013.01); *G02B 21/0088* (2013.01); *G02B 21/245* (2013.01)

(56) References Cited

FOREIGN PATENT DOCUMENTS

| | | | |
|---|---|---|---|
| DE | 2834204 A1 * | 3/1980 | ............. G02B 21/18 |
| DE | 2834204 A1 * | 3/1980 | ............. G02B 21/18 |
| DE | 100 56 384 A1 | 5/2002 | |
| EP | 0 207 485 A2 | 1/1987 | |
| EP | 1 849 861 A1 | 10/2007 | |
| FR | 1 588 938 A | 3/1970 | |
| FR | 2 468 925 A1 | 5/1981 | |
| WO | WO 98/42356 | 10/1988 | |
| WO | WO 95/00871 | 1/1995 | |
| WO | WO 97/02477 A1 | 1/1997 | |

OTHER PUBLICATIONS

Samuel T. Hess, et al., "Dynamic clustered distribution of hemagglutinin resolved at 40 nm in living cell membranes discriminates between raft theories", *PNAS* (2007); 104(44):17370-17375.
Samuel T.Hess, et al., "Ultra-High Resolution Imaging by Fluorescence Photoactivation Localization Microscopy", *Biophysical Journal* (2006); 91:4258-4272.
Hari Shroff, et al., "Dual-color superresolution imaging of genetically expressed probes within individual adhesion complexes", *PNAS* (2007), 104(51):20308-20313.
Rust, Michael J., et al., "Sub-diffraction-limit imaging by stochastic optical reconstruction microscopy (STORM)", *Nature Methods* (2006), 3:793-796.
Alexander Egner, et al., "Fluorescence Nanoscopy in Whole Cells by Asynchronous Localization of Photoswitching Emitters", *Biophysical Journal* (2007), 93:3285-3290.
Toprak, Erdal, et al., "Three-Dimensional Particle Tracking via Bifocal Imaging", *Nano Letters* (2007), 7(7):2043-2045.
Juette, Manuel F., et al., "Three-dimensional sub-100 nm resolution fluorescence microscopy of thick samples", *Nature Methods* (2008), 5(6):527-529.
Bo Huang, et al., "Three-Dimensional Super-Resolution Imaging by Stochastic Optical Reconstruction Microscopy", *Science* (2008), 319:810-813.
Jorg Bewersdorf, "3D Optical Superresolution: 4Pi Microscopy and Photoactivation Localization Microscopy", Presentation.
Hess, et al., "Dynamic clustered distribution of hemagglutinin resolved at 40 nm in living cell membranes discriminates between raft theories", PNAS (2007);104(44):17370-17375.

* cited by examiner

HIGH-RESOLUTION MICROSCOPE AND IMAGE SPLITTER ARRANGMENT

RELATED APPLICATIONS

The present application is a continuation application of U.S. patent application Ser. No. 13/518,108 filed on Jun. 21, 2012 which is a U.S. National Stage application of International PCT Application No. PCT/EP2010/007594 filed on Dec. 14, 2010 which claims priority benefit of German Application No. DE 10 2009 060 490.1 filed on Dec. 22, 2009, the contents of each are incorporated by reference in their entirety.

FIELD OF THE INVENTION

The present invention relates generally to the field of microscopy and more particularly to high-resolution microscopy.

BACKGROUND OF THE INVENTION

The background of the invention can be appreciated from the following literature:
[1] Betzig et al, Science 313, pp. 1642-1645 (2006);
[2] Hess et al., PNAS 104, pp. 17370-17375 (2007);
[3] Hess et al., Biophys J. 91, pp. 4258-427 (2006);
[4] Shroff et al., PNAS 104, pp. 20308-2031 (2007);
[5] Rust et al., Nature Methods 3, pp. 793-796 (2006);
[6] Egner et al., Biophys J. 93, pp. 3285-3290 (2007);
[7] Toprak et al., Nano Lett. 7, pp. 2043-2045 (2007);
[8] Juette et al., Nature Methods 5, p. 527 (2008); and
[9] Huang et al., Science 319, p. 810 (2008).

For some time now, various methods for overcoming the diffraction limit have been developed and applied in fluorescence microscopy (PALM, STED, Structured Illumination). A method for high-resolution fluorescence microscopy that is developing rapidly at present is based on highly precise localization of individual molecules. It is known that localization, that is, determination of the position of an individual fluorescent molecule, is not subject to diffraction limits (see references). This localization can be performed using wide-field high sensitivity cameras with a precision reaching into the nm range, if a sufficient number of photons of the molecule can be detected. In high-resolution microscopy based on localization, an image is composed from the molecule positions obtained in this manner. It is critical in this respect that only a subset of the molecules of the sample are in a fluorescent state, so that on average, the "nearest-neighbor" distance of the active molecules is always greater than the PSF of the microscope. This is achieved by using optically or chemically switchable fluorophores: in a densely marked region of a sample, stochastic subsets of fluorophores in the region of interest are switched by irradiation of a suitable conversion wavelength into the fluorescent state. The spot density is adjusted in such a way that the molecule positions can be localized continually. This optical switching method is used, for example, in Photo Activated Localization Microscopy (PALM). Variations of this fundamental method are described in detail in the literature [1-6].

Its variants (PALM, STORM, D-STORM, etc.) primarily differ in the selection of the fluorophores and the type of optical switching process.

However, all methods have in common that molecule localization is achieved by imaging on a highly sensitive camera (e.g. an EMCCD). The quasi-point light source (molecule) is represented by the point-spread function (PSF) of the microscope over several camera pixels. The precise position of the molecule on the x/y plane can now be determined either by fitting of the known PSF (Gaussian) or by determining the center of gravity, or by a combination of the two (Gaussian Mask Fit).

Typical localization precision ranges from 5 to 30 nm (depending on the experimental conditions); this then also represents approximately the lateral resolution of this method. The requirement that molecules should not be located too closely to one another on the one hand and that the examined structures should be represented as completely as possible, on the other, means in practice that many individual images (typically 20,000) must be taken of the sample. In each image, the positions of the molecules that are active at that point in time are determined and stored. Thus, considerably longer calculation or analysis times (depending on the algorithm and computer system used) are added to the already considerable image recording time for 20,000 images before the actual high-resolution image is available.

The method of high resolution based on localization described above is, however, limited to surfaces of two dimensions, since the localization of each dye molecule is incomparably more complex in the third spatial dimension (z-direction). Several approaches are known from the literature that will be briefly discussed below.

Astigmatism/Cylindrical Lens (See Reference [9]):

In this approach, a weak cylindrical lens is inserted into the detection-beam path, which leads to an astigmatic PSF. Accordingly, the image of the molecule is elliptically distorted when the molecule is located above or below the symmetry point of the PSF. Information can then be extracted about the z-position of the molecule from the orientation and magnitude of the distortion. A problem with this method is that the local environment and the orientation of the molecular dipole can also result in a distortion of the spot of the molecule (see above references). These molecules would then be assigned a false z-value depending on their orientation.

Detection on Two Planes:

In this technique, a 50/50 beam splitter is inserted into the detection beam path that splits (duplicates) the image into two partial images. These two images are either displayed on two identical cameras or side-by-side on a camera chip. An optical difference in path lengths is introduced into one of the two partial beam paths so that two object planes develop from the two partial beam paths, apart from each other in the z-direction by approximately half to one z-PSF (700 nm). The z-position for molecules located between these two planes can now be determined, e.g. by means of subtracting the two partial images of the molecule and/or by fitting a three-dimensional PSF.

For this method, either two highly sensitive cameras are required or both images must be arranged side-by-side on a camera chip. The latter will naturally result in a limitation of the image field. Furthermore, both variants require precise alignment of the beam paths or calibration measurements in order to ensure sub-pixel-precise overlapping of the two partial images.

The methods described above for localization in the x/y plane and/or in the z-direction can be used not only for high-resolution microscopes, but also for particle or molecule tracking, respectively. This applies accordingly to the potential solutions presented below.

Various Approaches are Known for Detection on Multiple Planes:

The following are examples:

Beam splitting and generation of two object planes through different image distances: See Bewersdorf et al. [8], Toprak et al. [7]

AT 402 863 B describes beam splitting in the detection using two cameras, at least one of which can be moved axially to change the object distance. The purpose is a comparative representation of images based at different object depths.

WO 95/00871 describes chromatic beam splitting on two detectors for 3D representation of objects.

U.S. Pat. No. 5,982,497 describes chromatic beam splitting and laterally offset imaging at the same object and image distance for representation of two or more color channels on one image sensor.

References [7] and [8] are most relevant for high-resolution depth localization of individual molecules in the z-direction.

However, the solutions described in the above references have the following disadvantages and limitations:

- Oblique incidence on the image sensor causes distortions of the PSF depending on the z-position; the center of gravity is laterally dependent on the z-position;
- The imaging scale changes as a function of the z-position;
- Splitting cannot be adjusted, meaning that the optimal working point cannot be adjusted for different microscope objectives;
- If an adjustment were (theoretically) made (such as by the mirror method described in [8]), it would be impossible to set the z-splitting on both planes to "zero," due to a longer beam path in air;
- An adjustment made in this way would shift the moved object plane into the cover glass at an increased z-splitting when measuring objects near the cover glass in high resolution, requiring refocusing of the entire system.

The problem to be overcome by the present invention therefore is splitting a microscope image into two partial images on two partial areas of an image sensor while avoiding the disadvantages and limitations mentioned above.

SUMMARY OF THE INVENTION

The problem of the prior art, and therefore the objectives of the invention are solved by the subject matter of the independent claims. Particularly advantageous developments are the subject matter of the dependent claims.

The invention can be used in a high-resolution microscope for three-dimensional determination of the position of objects, particularly individual fluorophores, preferably for fluorescent microscopy in high spatial resolution of a sample marked with marking molecules, which can be activated or switched by a signal in such a way that only in the activated or switched state can they be excited to emit fluorescent radiation. The method of the invention includes:

a) Introducing the signal to the sample in such a way that only a subset of the marker molecules present in the sample are activated, with sub-regions existing in the sample in which activated marker molecules have a minimum distance from their nearest neighboring activated marker molecules greater than or equal to a distance that represents a predetermined optical resolution;

b) Excitation of the activated molecules to emit fluorescent radiation;

c) Detection of fluorescent radiation with a predetermined optical resolution; and d) Generation of an individual image from the luminescent radiation recorded in step c), wherein the geometric locations of the marker molecules emitting the fluorescent radiation are determined with a spatial resolution enhanced beyond the predetermined optical resolution;

wherein the steps are repeated several times, and the multitude of individual images obtained in this manner are combined to an overall image.

BRIEF DESCRIPTION OF THE DRAWINGS

FIG. 1(a) shows an enlarged view of the variable image splitter module BM according to the invention.

FIG. 1(b) shows enlarged point images of molecules 1, 2, 3, from object planes E1, E2, respectively, on sensor halves S1 and S2 of FIG. 1.

The reference symbols appearing in the foregoing drawings have the following meanings:

E1, E2: Object planes;
BM: Image splitter module;
O: Objective;
Dic1: Main dichroic splitter;
L1: Light source
EF: Emission filter
TL: Cylindrical lens;
SP: Deflection mirror;
B: Diaphragm (telecentric diaphragm);
L1, L2: Lens groups;
Dic 2: Dichroic splitter for optional diversion;
BS: Beam-splitter cube;
P1: Dual deflection prism, adjustable perpendicular to the optical axis;
P2: Deflection prism;
DE: Wide field detector;
S1, S2: Sensor halves;
e1, e2: Image planes.

DETAILED DESCRIPTION OF THE EMBODIMENTS

Figure 1:
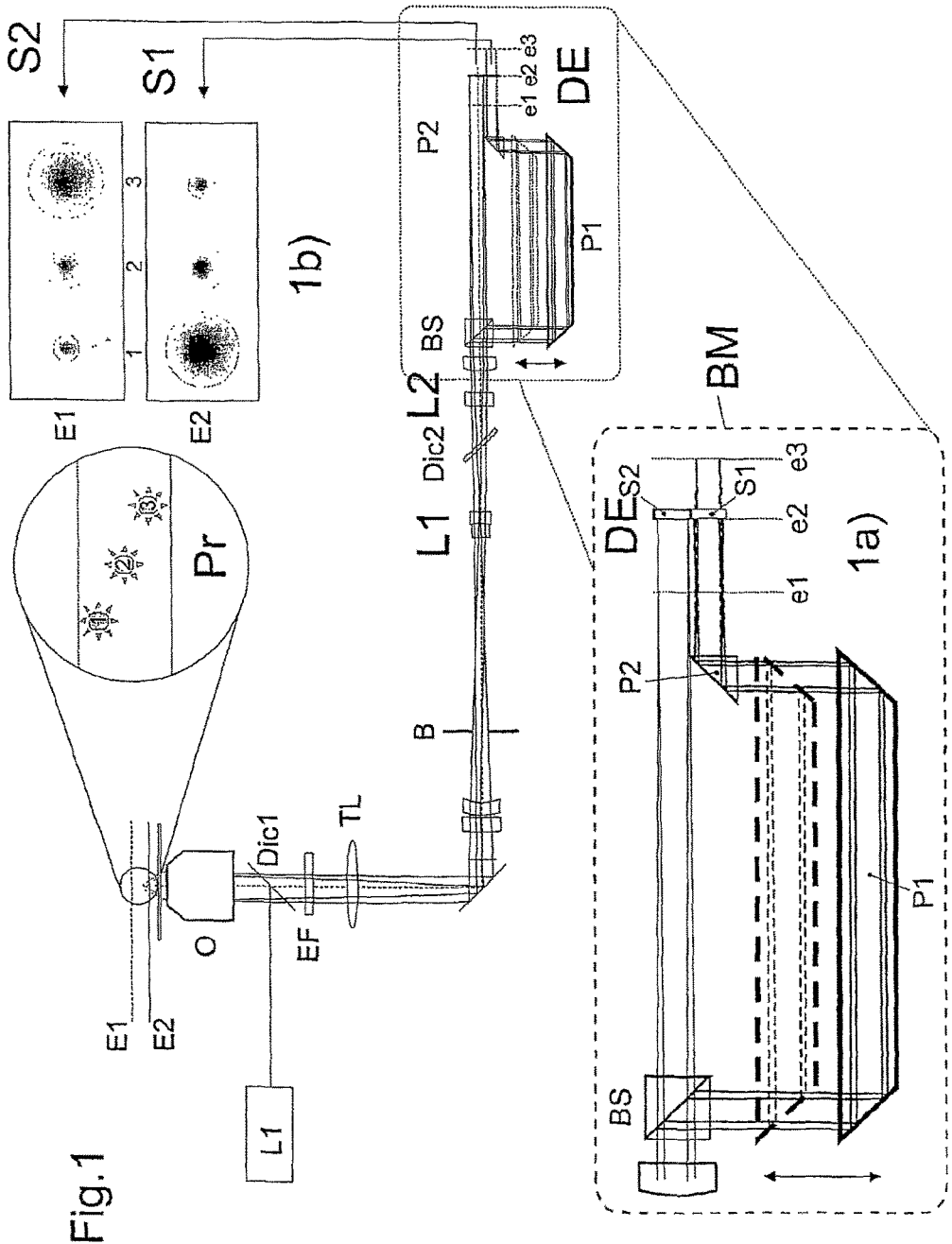
FIG. 1 is a sketch of a variable image splitter module for z-splitting as presented herein.

FIG. 1 shows a wide field beam path with a dilated light source and a spatially resolved planar detector such as a CCD camera.

The light from light source L1 reaches the sample Pr (reflected) via Dic 1 and the objective O. The reflected and fluorescent sample light passes through the objective in the direction of detection. Selection of the desired portion of the light is performed at splitter Dic 1 through filter EF, i.e. the reflected light is suppressed, and only the fluorescent light passes on in the direction of detection. The sample light reaches the arrangement according to the invention consisting of BS, P1, and P2 and then the detector DE via SP, L1, and L2, E1 and E2 are different object planes in the sample Pr.

FIG. 1a shows an enlarged view of the variable image splitter module BM according to the invention. An image of the sample Pr is split via the beam-splitter cube BS into two partial images on the detector DE. The prism P1 is moved by a motor perpendicular to the optical axis to set the splitting of the two object planes. The displaced partial image is in turn reflected back into the direct beam path via P2 (fixed), spatially offset with respect to the direct beam path, i.e., laterally offset on DE.

The invention will be explained in greater detail below with reference to image planes e1 to e3 of one and the same object plane in Pr.

The dashed position of P1 indicates the shortest possible position of BM, the image plane e3 obtained in this way would be behind the detector DE. Image plane e2 of the undeflected partial image lies on the sensor (partial area S2 of the sensor). By moving the prism P1 outward into the lower position shown in FIG. 1a, the path is lengthened and the image plane e1 moves toward the front (opposite to the light path).

It follows from this that an object (molecule) located in object plane E2 will be displayed in focus on sensor half S2 and out of focus on sensor half S1. This applies accordingly to an object located in object plane E1 or between E1 and E2. E1 would be in focus on S1 and E2 would be in focus on S2. Everything else would be out of focus in the same prism position.

FIG. 1b shows enlarged point images of molecules 1, 2, 3, from object planes E1, E2, respectively, on sensor halves S1 and S2 of FIG. 1.

It is apparent that molecules arranged in different planes, respectively (1 in E1 and 3 in E2) in S1 (molecule 1) and S2 (molecule 3) are detected in focus while molecule 2 is detected similarly out of focus each time, because it is obviously located between E1 and E2.

The precise locations of the molecules in the z-direction within the sample can be inferred from their sizes on the detector sections. The figure also indicates the beam paths of two molecules, both located in object plane E2.

The diaphragm B defines the reduced half of the image section (equivalent to the size of the sensor halves S1 and S2) and prevents light from outside this area from impinging on the two partial beam paths.

Splitting into two partial images occurs at the 50/50 beam-splitter cube BS. The problem of focusing the deflected partial image onto an image plane different from the directly displayed partial image is solved by prism P1. This prism P1 extends the focal length of the respective rays compared to the corresponding path through the air; therefore it should preferably be made of a highly refractive glass, in order to obtain as large an operating range as possible. These rays are then once more reflected parallel to the direct beam path via prism P2, and directed onto the image sensor DE in section S1.

With the back focal extension after the last optics/lens L2 in the prism P1, it can be ensured by selecting the length of the prism that, in spite of an inevitably longer beam path of the deflected partial image, both partial images from different object planes E1, E2 are simultaneously imaged in focus on the detector DE. The z-displacement of the focal planes of the two partial images from different object planes can be set in the sample by moving prism P1 perpendicular to the optical axis of the direct beam path. In this way, the splitting can advantageously be adjusted to different objectives, for instance. This can now be done without secondary focusing of the system, since the system has been designed so that a "zero" adjustment can be set and the second focal area can be moved into the sample (and not into the cover glass), particularly when observing on the surface of the cover glass.

In another arrangement, in which the glass path of the prism P1 is left out and only two deflection mirrors that are jointly displaceable perpendicular relative to the optical axis are used, two different object planes can also be advantageously imaged in focus on the camera.

However, zero compensation would not be achieved, due to the lateral path, and one would move further into the "cover glass" when the mirror was displaced laterally. In order to vary the second object plane in the sample space, the splitting of the object plane would have to be adjusted via the mirrors and then refocused at the objective in such a way that the cover glass is once more focused on the detector via the deflection. However, this arrangement described is still within the scope of the invention disclosed here.

Exchanging prism P1 for another prism with different glass paths is possible according to the invention.

Imaging from the object onto the detector via lens L2 in conjunction with the optics of L1 left of beam splitter Dic 2 is advantageously telecentric overall. An adjustable, preferably rectangular diaphragm B in an intermediate aerial image serves to define a rectangular image area, split via P1, P2, and to suppress fluorescent and stray light from the field areas outside this new area.

For multi-color experiments, a second emission wavelength can be deflected via dichroic splitter Dic 2, and this beam path can also be used for high-resolution localization using a second, preferably identical, z-splitting module and another detector. Any axial chromatic errors of the objective or other chromatic errors influencing the z-localization of individual molecules can be compensated by adjusting the splitting for the second color channel.

FIG. 2a) shows another embodiment of a module for splitting a camera image into 4 partial images of identical intensity for z-high resolution. FIG. 2a), left, shows an embodiment with separate mirrors and beam splitters. A first splitter T1, here splitting at a ratio of 25/75 transmission and reflection, respectively, guides a portion of the light to the area Q1 of detector DE4.

A second portion is reflected at T1 and guided via a mirror S1 in the direction of a second splitter T2 with a ratio of 66/33. It allows a portion of the light to pass in the direction of area Q2 of DE4 and reflects a portion in the direction of a mirror S3, which deflects the light in the direction of the 50/50 splitter T3. A portion passes through T3 to area Q3 of DE 4 and a portion is deflected via S3 in the direction of area Q4 of DE 4.

Four evenly displaced image and/or object planes result from the By splitting the Z-planes in the monolithic layout by one "cube length" of a beam splitter cube one obtains four equally displaced images and object planes, whereby quadrant Q1 of DE4 sees the image by direct transmission, quadrant Q2 sees it displaced by "one standard distance" (=1 beam splitter cube length in the monolithic design, on the right), quadrant Q3 by two and quadrant Q4 by three distances.

The splitter ratios of the three beam splitters shown here ensure without any limitation that all 4 quadrants preferably detect the same intensity.

FIG. 2b) shows side, top, and perspective views of a monolithic design with 3 beam-splitter cubes for T1-T3 and 3 mirrored prisms for S1-S3. The arrangement in FIGS. 2a) and b) is also suited for a telecentric detection beam layout as described with reference to FIG. 1.

Figure 2:
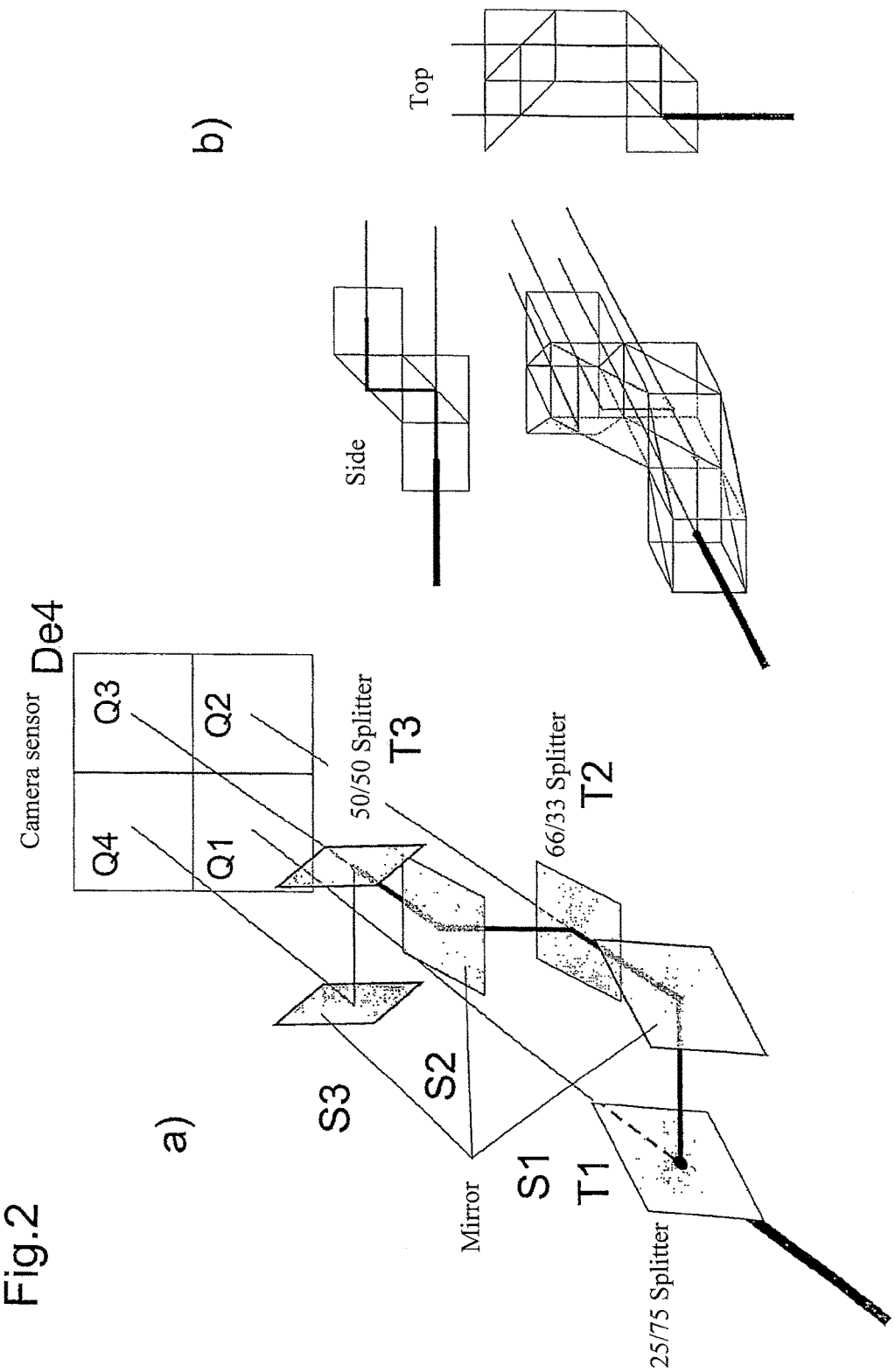
FIG. 2(a) shows another embodiment of a module for splitting a camera image into 4 partial images of identical intensity for z-high resolution.
FIG. 2(b) shows side, top, and perspective views of a monolithic design with 3 beam-splitter cubes for T1-T3 and 3 mirrored prisms for S1-S3.

The advantages of the arrangement according to the invention in FIG. 2 particularly include that advantageously four support points are provided by four images of four sample levels for the z-determination by Gaussian Mask Fit, thereby allowing a more precise z-determination in a larger operating range.

In addition, the square sensor format of the highly sensitive EMCCD cameras is utilized even more efficiently.

Figure 3:
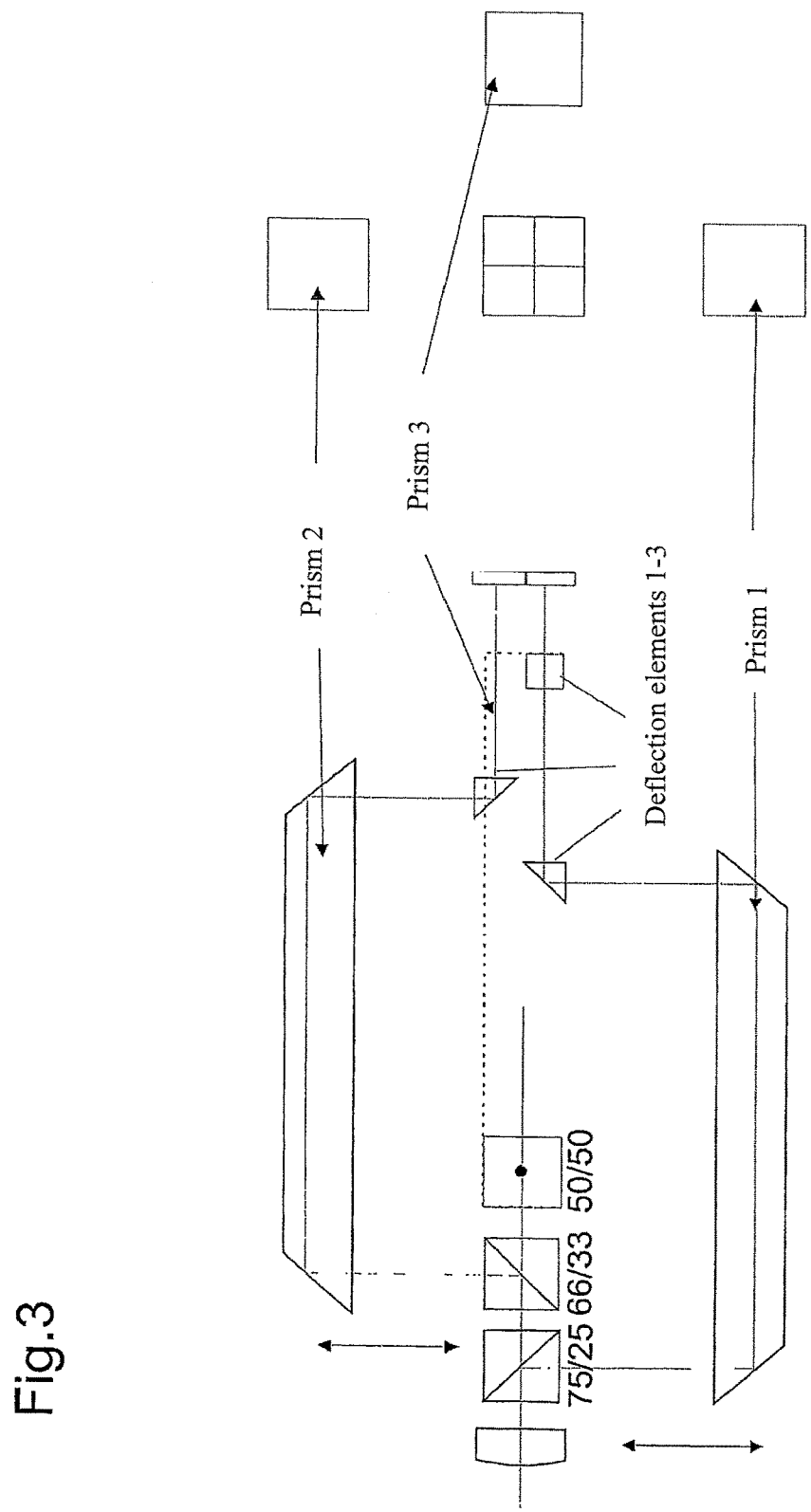
FIG. 3 illustrates a combination of an embodiment according to FIG. 2 with movable prisms according to FIG. 1.

FIG. 3 illustrates a combination of an embodiment according to FIG. 2 with movable prisms according to FIG. 1.

A view from the sensor is shown on the right, a top view on the left.

Instead of the mirrors S1-S3 in FIG. 2, prisms 1-3 are provided here, which define a light path running parallel to the optical axis through a medium of higher refractive index. Compared to FIG. 2, additional deflection elements 1-3 are used here for redeflection into the respective partial beam path.

Each of the three prisms 1-3 that are adjustable perpendicular to the optical axis (direction of light beam) is provided for one quadrant Q2-4 of the sensor (FIG. 2); the fourth quadrant Q1 is irradiated by the direct beam. Each prism can now be set to a different displacement of planes.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A microscope having an illumination beam path with wide-field illumination of a sample comprising, a first detection-beam path, a spatially resolved planar detector located within said first detection-beam path, said planar detector having a detection plane, a first part of detection light coming from said sample reaching said detection plane via said first detection-beam path or from an image splitter arrangement within said microscope, at least a second part of said detection light coming from said sample being deflected out of the detection-beam path in order to lengthen the optical path length for the second part of said detection light, deflection means associated with said detection-beam path, for guiding said second part of said detection light along at least a second detection-beam path, a further deflection means for deflecting said second detection beam path of said detection light back in the direction of detection in such a way that detection light is caused to be incident on at least two distinct partial areas of said detection plane, wherein at least the second part of the detection light reaches said detection plane in a different area of said detection plane than said first part so that two different focal planes are simultaneously imaged onto different areas of the detection plane, and an optical element is designed to be movable at an angle to the optical axis of the first detection beam path in order to adjust the length of the optical path.

2. The microscope according to claim 1 wherein said sample is marked with marking molecules which can be activated or switched by a signal such that only in the activated or switch state can they be excited to emit fluorescent radiation, and further comprising a source of radiation for directing a beam of radiation onto said sample thereby activating said marked molecules producing reflected fluorescent detection light.

3. The microscope according to claim 2, wherein a prism is provided at least in the second detection beam path after a first beam deflection for deflection in a direction parallel to the first detection-beam path in order to lengthen the path length and for reverse deflection.

4. The microscope according to claim 3, wherein the parallel part of the second detection beam path passes through the prism.

5. The microscope according to claim 3, wherein the prism is designed to be moved perpendicularly to the optical axis for adjusting the optical path length.

6. The microscope according to claim 2, further comprising a telecentric beam path from the sample to the detector.

7. The microscope according to claim 2, wherein the diversion of at least the second detection beam path occurs telecentrically in the direction of the detector plane or is located in a telecentric portion of the detection beam path.

8. The microscope according to claim 2, wherein said prism is a glass prism.

9. A microscope having an illumination beam path with wide-field illumination of a sample, comprising a first detection beam path that includes a spatially resolved planar detector having a detection plane, a first part of detection light coming from said sample reaching said detection plane via said first detection beam path or from an image splitter, wherein at least a second part of the detection light coming from the sample is diverted out of the detection beam path in order to lengthen the optical path length for the second part of said detection light, and, via deflection means associated with the detection-beam path, is guided in at least a second detection beam path of said detection light and, via further deflection means is deflected back in the direction of the detection in such a way that detection light is caused to be incident on at least two distinct partial areas on the detection plane so that said second part of said detection light reaches said detection plane in a different area of said detection plane than said first part so that two different focal planes are simultaneously imaged onto different areas of the detection plane, and wherein at least one part of the deflection means is designed for being movable at an angle to the optical axis of the first detection beam path for adjustment of the optical path length.

10. The microscope according to claim 9 wherein said sample is marked with marking molecules which can be activated or switched by a signal such that only in the activated or switch state can they be excited to emit fluorescent radiation, and further comprising a source of radiation for directing a beam of radiation onto said sample thereby activating said marked molecules producing reflected fluorescent detection light.

11. The microscope according to claim 10, wherein said angle is 90°.

12. A microscope having an illumination beam path with wide-field illumination of a sample, comprising a first detection beam path that includes a spatially resolved planar detector having a detection plane, a first part of detection light coming from said sample reaching said detection plane via said first detection beam path, or from image splitter, wherein at least a second part of the detection light coming from the sample is diverted out of the detection beam path in order to lengthen the optical path length for the second part of said detection light, and, via deflection means associated with the detection-beam path, it is guided in at least a second detection beam path of said detection light and, via further deflection means, is deflected back in the direction of the detection in such a way that detection light is caused to be incident on at least two distinct partial areas on said detection plane, wherein a splitting takes place into four detection beam paths that impinge upon one or more detectors at an offset to one another, so that different focal planes are simultaneously imaged onto different areas of the detection plane via partially transparent mirrors and deflection elements.

13. The microscope according to claim 12 wherein said sample is marked with marking molecules which can be activated or switched by a signal such that only in the activated or switch state can they be excited to emit fluorescent radiation, and further comprising a source of radiation for directing a beam of radiation onto said sample thereby activating said marked molecules producing reflected fluorescent detection light.

14. The microscope according to claim 13, wherein three partially transparent mirrors and three deflection elements are provided for splitting, and the partially transparent mirrors exhibit splitting ratios of 25/75, 66/33, and 50/50 between transmitted and reflected radiation.

15. A method for using a microscope having an illumination beam path with wide-field illumination of a sample which is marked with marking molecules which can be activated or switched by a signal such that only in the activated or switch state can they be excited to emit detection light, comprising a first detection beam path that includes a spatially resolved planar detector having a detection plane, a first part of detection light coming from said sample reaching said detection plane via said first detection beam path or from an image splitter, wherein at least a second part of the detection light coming from the sample is diverted out of the detection beam path in order to lengthen the optical path length and, via deflection means associated with the detection-beam path, is guided in at least a second detection beam path and, via further deflection means, is deflected back in the direction of the detection in such a way that detection light is caused to be incident on at least two distinct partial areas on said detection plane so that said second part of said detection light reaches said detection plane in a different area of said detection plane than said first part, and wherein at least one part of the deflection means is designed for being movable at an angle to the optical axis of the first detection beam path for adjustment of the optical path length, wherein the method comprises the following steps:
  (a) introducing the signal to the sample in such a way that only a subset of the marker molecules present in the sample are activated, with sub-regions existing in the sample in which activated marker molecules have a minimum distance from their nearest neighboring activated marker molecules greater than or equal to a distance that represents a predetermined optical resolution;
  (b) exciting of the activated molecules to emit fluorescent radiation;
  (c) detecting of fluorescent radiation with a predetermined optical resolution; and
  (d) generating of an individual image from the luminescent radiation recorded in step 3) wherein the geometric locations of the marker molecules emitting the fluorescent radiation are determined with a spatial resolution enhanced beyond the predetermined optical resolution; wherein the steps are repeated several times, and the multitude of individual images obtained in this manner are combined to an overall image.

16. A method for using a microscope having an illumination beam path with wide-field illumination of a sample which is marked with marking molecules which can be activated or switched by a signal such that only in the activated or switch state can they be excited to emit detection light, comprising a first detection beam path that includes a spatially resolved planar detector having a detection plane, a first part of detection light coming from said sample reaching said detection plane via said first detection beam path, or from image splitter wherein at least a second part of the detection light coming from the sample is diverted out of the detection beam path in order to lengthen the optical path length and, via deflection means associated with the detection-beam path, it is guided in at least a second detection beam path and, via further deflection means, is deflected back in the direction of the detection in such a way that detection light is caused to be incident on at least two distinct partial areas on said detection plane, wherein a splitting takes place into four detection beam paths that impinge upon one or more detectors at an offset to one another via partially transparent mirrors and deflection elements, wherein the method comprises the following steps:
  (a) introducing the signal to the sample in such a way that only a subset of the marker molecules present in the sample are activated, with sub-regions existing in the sample in which activated marker molecules have a minimum distance from their nearest neighboring activated marker molecules greater than or equal to a distance that represents a predetermined optical resolution;
  (b) exciting of the activated molecules to emit fluorescent radiation;
  (c) detecting of fluorescent radiation with a predetermined optical resolution; and
  (d) generating of an individual image from the luminescent radiation recorded in step 3) wherein the geometric locations of the marker molecules emitting the fluorescent radiation are determined with a spatial resolution enhanced beyond the predetermined optical resolution; wherein the steps are repeated several times, and the multitude of individual images obtained in this manner are combined to an overall image.

* * * * *